United States Patent [19]

Mizrach et al.

[11] Patent Number: 5,589,209
[45] Date of Patent: Dec. 31, 1996

[54] METHOD FOR A NON-DESTRUCTIVE DETERMINATION OF QUALITY PARAMETERS IN FRESH PRODUCE

[75] Inventors: Amos Mizrach, Rishon-Le-Zion; Naftali Galili, Afula; Giora Rosenhouse, Haifa, all of Israel

[73] Assignee: State of Israel, Ministry of Agriculture, Bat Dagan, Israel

[21] Appl. No.: 427,219

[22] Filed: Apr. 24, 1995

[30] Foreign Application Priority Data

Apr. 24, 1994 [IL] Israel ................................. 109406

[51] Int. Cl.⁶ .................................................. G05B 1/00
[52] U.S. Cl. ............................................ 426/231; 426/238
[58] Field of Search .................................. 426/231, 238, 426/615; 73/599

[56] References Cited

U.S. PATENT DOCUMENTS

| | | | |
|---|---|---|---|
| 2,538,444 | 1/1951 | Mars | 73/599 |
| 2,966,057 | 12/1960 | Heller | 73/599 |
| 5,095,442 | 3/1992 | Salvado | 73/599 |

FOREIGN PATENT DOCUMENTS

| | | | |
|---|---|---|---|
| 1336988 | 9/1987 | U.S.S.R. | 426/238 |

OTHER PUBLICATIONS

"Half–Cut Fruit Response to Ultrasonic Excitation" by Amos Mirach, American Society of Agricultural Engineers, Paper 923017, Jun. 21–24, 1992.

"Acoustical, Mechanical, and Quality Parameters of Winter–Grown Melon Tissue" by A. Mizrach et al, American Society of Agricultural Engineers, vol. 34(5), Sep.–Oct. 1991, pp. 2135–2138.

"Determination of Fruit and Vegetable Properties by Ultrasonic Excitation" by A. Mizrach et al, American Society of Agricultural Engineers, vol. 32(6), Nov.–Dec., 1989, pp. 2053–2058.

*Primary Examiner*—George Yeung
*Attorney, Agent, or Firm*—Lowe, Price, LeBlanc & Becker

[57] ABSTRACT

A method and a system for a non-destructive determination of quality parameters in fresh produce. Ultrasonic sound waves are transmitted into the produce from a transducer and are received by a nearby transducer, both gripped via special arrangement cage, allowing local ultrasonic tests on the produce. Various acoustical parameters such as wave velocity and signal attenuation of the detected sound waves are analyzed in conjunction with the maturity of the sample.

17 Claims, 4 Drawing Sheets

5,589,209

METHOD FOR A NON-DESTRUCTIVE DETERMINATION OF QUALITY PARAMETERS IN FRESH PRODUCE

FIELD OF THE INVENTION

The present invention relates to a method and a system for a non-destructive determination of quality parameters in fresh produce in which a burst of ultrasonic excitation is transmitted along a sound path through the tissue of fresh produce like fruits or vegetables. After the sound waves have passed through the tissue, they are detected and analyzed to determine their sound speed and attenuation, which then indicates the quality parameters of the fresh produce.

BACKGROUND OF THE INVENTION

Determination of ultrasonic parameters such as sound velocity and attenuation in engineering materials and many biological tissues have been well-documented in literature, e.g., "Physical Principles of Ultrasonic Diagnosis" by P. N. T. Wells, (Academic Press, New York, 1969). Sound end particularly ultrasonia sound have been used in numerous devices to determine various physical characteristics of materials, but these Known devices do not relate to a method for determining the ripeness or maturity of fruits end/or vegetables. For example, U.S. Pat. Nos. 2,966,057 and 2,538,444 disclose systems that measure attenuation of ultrasonic energy when it passes through a medium. Despite the wide use and success of these methods in industry and medicine, very little has been done to employ this technique for testing fresh food produce.

The main problems associated with the application of this technique are:

a) Fruit tissue is an inhomogeneous material.

b) Fruit tissue is a highly-attenuative material for high frequency ultrasonic signals.

c) Measuring time end detection of wave velocity and internal defects is difficult at low frequencies.

Mizrach et al. (Mizrach, A., N. Galili, and G. Rosenhouse, 1989. Determination of fruit and vegetable properties by ultrasonic excitation. Transaction of the ASAE, 32(6): 2053–2058. Mizrach, A., Galili, G. Rosenhouse, and D. C. Teitel, 1991. Acoustical, mechanical and quality parameters of winter grown melon tissue. Transactions of ASAE, 34(5):2135–2138. Mizrach, A., N. Galili, and G. Rosenhouse, 1992, Half-cut fruit response to ultrasonic excitation. ASAE Paper No. 923017. American Society of Agricultural Engineers, St. Joseph, Mich.) revising previous work, evaluated the use of low-frequency ultrasonic excitation for the determining the quality of fruit tissue and concluded that ultrasonic testing is a potential technique for the non-hazardous measurement of internal quality and latent defects in fruits and vegetables.

However, none of these previously proposed techniques are suitable for non-destructive, whole-fruit testing. In many kinds of fruits, the attenuation of sound prevents it from passing through the entire fruit. Hence, local ultrasonic tests over the peel of the fruit were performed experimentally, assuming that the internal fruit tissue next to the peel, effects the peel response.

Preliminary investigation on local testing of ultrasonic surface waves in the peel of a whole fruit was performed by the inventors. It was found that the acoustical parameters of some whole-fruits related to the ripening process and the changes in the mechanical and quality parameters of the fruit flesh.

SUMMARY OF THE INVENTION

The present invention relates to a method and a system for a non-destructive determination of quality parameters in fresh produce. The system and method of the present invention provides an ultrasonic determination of quality parameters like firmness, ripeness, crispness, and the like in fresh produce such as tissue sample, peel, and/or a whole-fruit or vegetable, where the attenuation of sound prevents it from passing through the entire fruit.

The method and system according to said invention uses ultrasonic sound waves transmitted into the produce from a transducer and received by a nearby transducer (or transducer), both gripped in a special arrangement cage, allowing local ultrasonic tests on the produce. More specifically the invention relates to a method for determining quality parameter of fresh produce using ultrasonic sound parameters. Furthermore, the invention provides a system for determining quality parameters of fresh produces using ultrasonic sound parameters.

DETAILED DESCRIPTION OF THE PREFERRED EMBODIMENT

The present invention will be further clarified and exemplified by description of the preferred embodiments of the present invention. These preferred and alternative embodiments are illustrated in FIGS. 1–4 and do not intend to limit the scope of the present invention.

Figure 1:
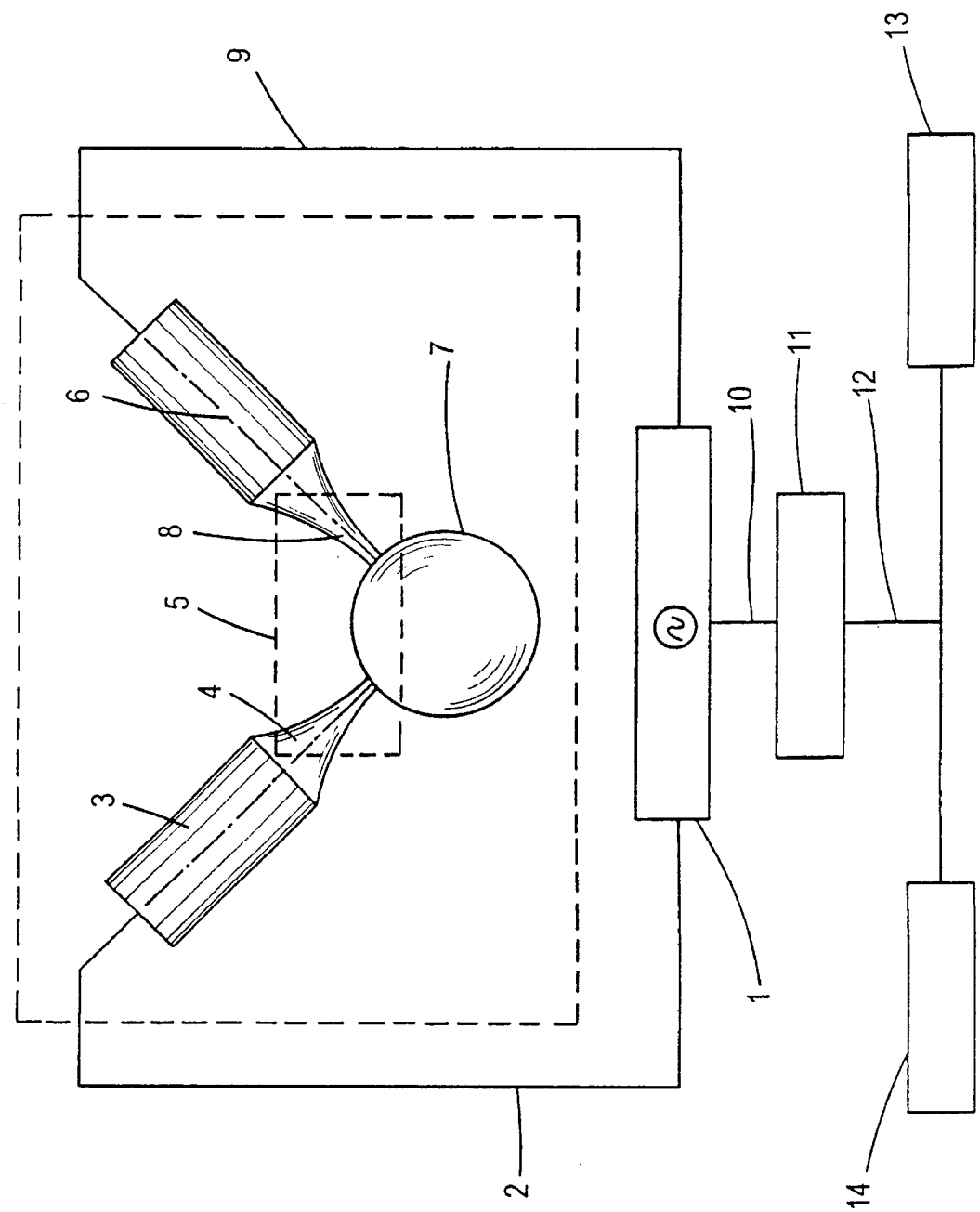
FIG. 1 is a schematic view of the system according to the present invention embodying the transducer configuration for velocity and attenuation measurements of tissue specimens of the present invention.

FIG. 1 shows a schematic diagram representing one form of the present invention. The diagram includes a pulser-receiver (1) that generates an electrical pulse at a frequency of 50-kilohertz on the line (2). In this particular embodiment, a Krautkramer Model USA 33 pulser-receiver is used as an excitation device. Line (2) is connected to a source transducer (3) for production of ultrasonic sound. In this particular embodiment a US 0.5 Model is used, but it will be understood that other sound transducers may be used. The transducer (3) produces an ultrasonic tone burst in response to the electrical signal received on the line (2).

The source transducer (3) is connected to energy concentrator (4) both contained within a housing unit (5) whose function is to isolate the transducer (3), concentrator (4) and other equipment. A receiving transducer (6) is connected to an energy concentrator (8) and both are positioned on the other side of the housing unit (5) from the source transducer (3).

According to the method and the system of the present invention, two or more receiving transducers may also be connected to the energy concentrator and positioned at different predetermined distances from the source transducer.

The sample (7) is positioned so that the wound beam produced by the transducer (3) will travel through the concentrator (4), and the fruit sample (7) and will be received through the concentrator (8) by the receiving transducer (6). In this embodiment, the energy concentrator (8) is identical to the energy concentrator (4) and the two concentrators are positioned apart at a distance of approximately 5 mm, creating a specific angle between them, the axes of the transmitter, and the receiver. However, relative motion of the heads to perform larger gape between the edges is allowed, while applying constant force on the fruit. The angle between the axes of the transmitter and the receiver can be changed as well.

The sample (7) is in touch with the two concentrators (4) and (8) (FIG. 1) and the sound beam produced by the transducer (3) in this embodiment is focused on a cylindrical-edge of approximately 5 mm in diameter. Other kinds end contours of edges are also possible.

Figure 2:
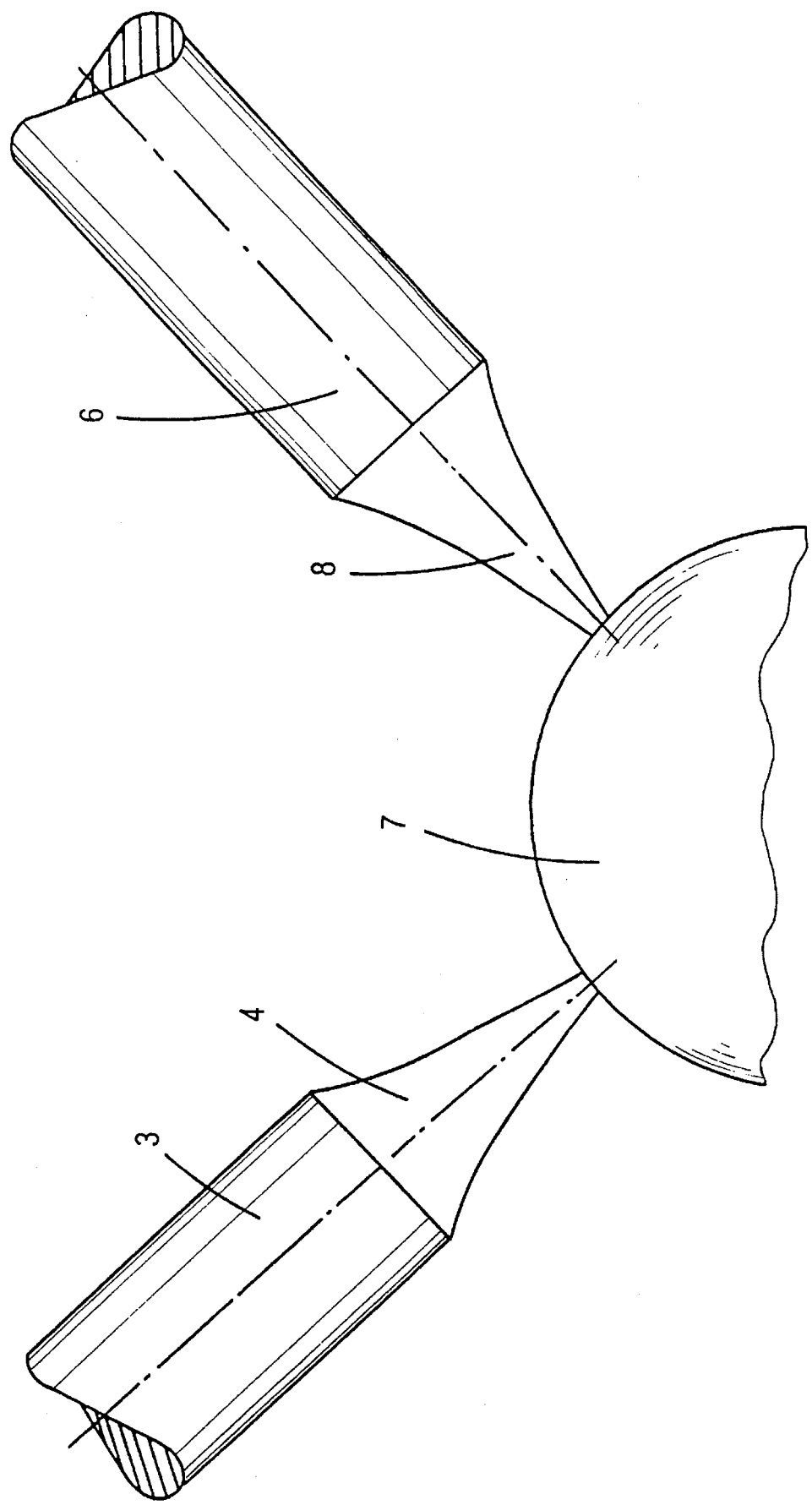
FIG. 2 is a detailed view of the transducer and cylindrical-edge, in this particular embodiment.

FIG. 2. This is an enlargement of the cylindrical-edge of approximately 5 millimeters.

The sound signal received by the transducer (6) is converted to an electrical signal and is applied through the line (9) to the pulser-receiver (1). The electronic signal received in the pulser-receiver (1) is applied through the line (10) to a microprocessor controlled serial interface (11) which allows transfer of the digital read-out of echo amplitude, the pulse transmit time and the actual instrument gain through the line (12) to an external computer (13). The computer analyzes the signal to determine the velocity and attenuation of the ultrasonic burst through sample tissue (7). The signal on the line (12) may also be applied to a recorder (14) which may be a conventional magnetic, tape recorder, or any other conventional recorder, which will record the output appearing on the line (12) for subsequent analysis.

The computer (13) will display results of velocity and attenuation corresponding to changes in firmness for various varieties of fruits or vegetables. This makes it possible to classify fruit according to firmness into several maturity groups.

Figure 3:
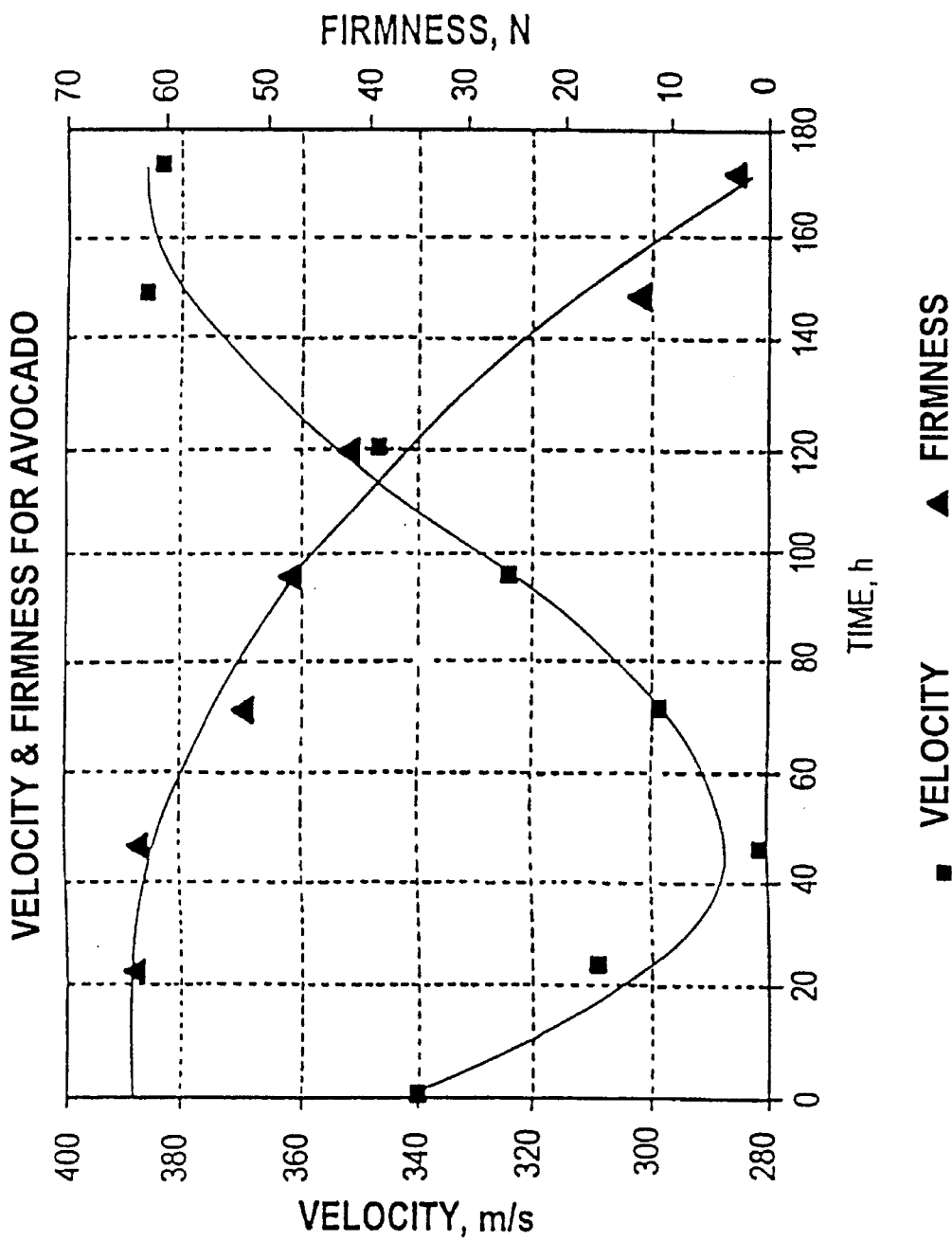
FIG. 3 is a graph of the surface velocity of the ultrasonic signal in the peel and vecinity of the peel of a whole avocado fruit vs. time. This graph also presents the firmness of the fruit vs. time.
Figure 4:
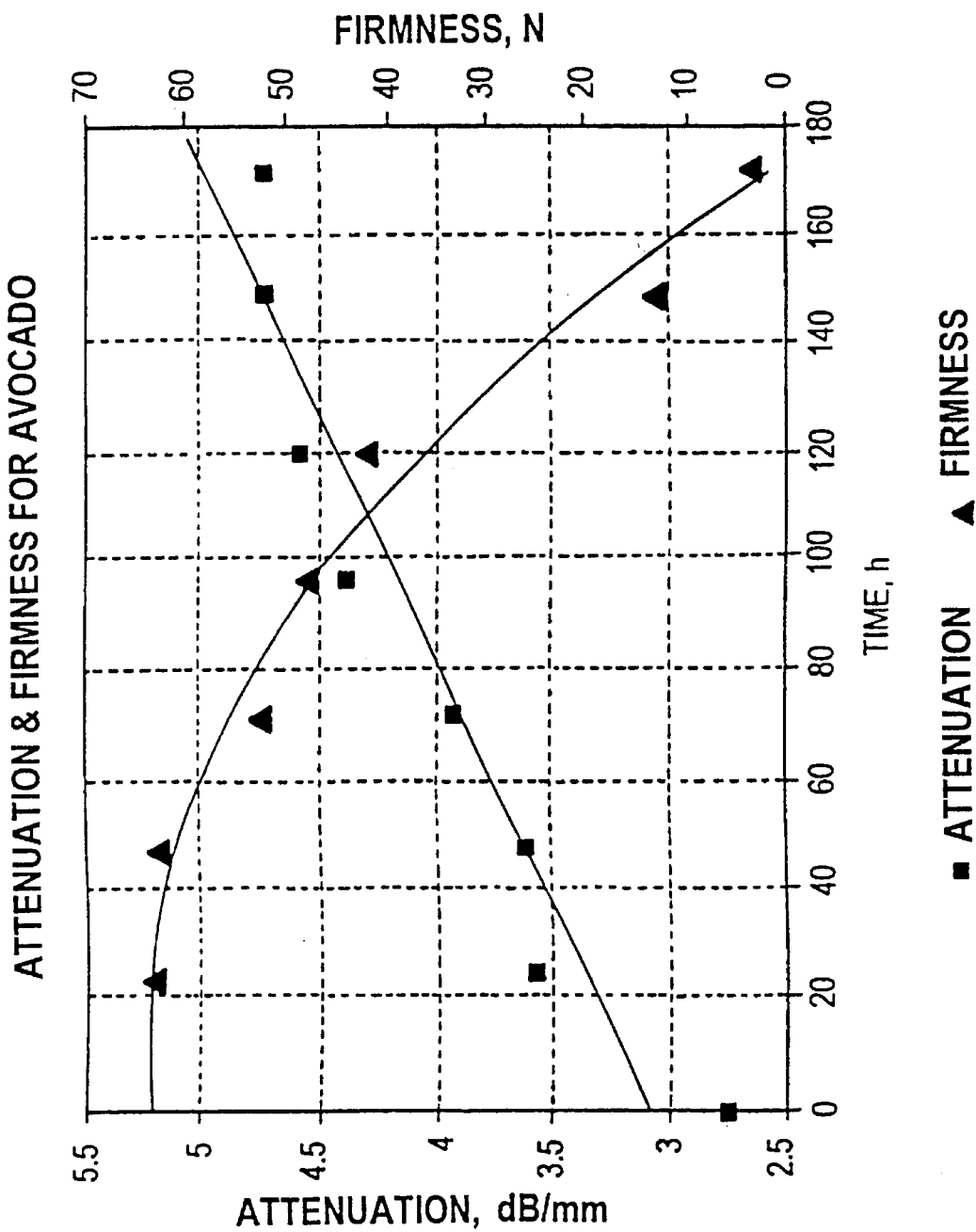
FIG. 4 is a graph of the apparent attenuation of the ultrasonic signal in the peel and vecinity of the peel of a whole avocado fruit vs. time. This graph also presents the firmness of the fruit vs. time.

FIGS. 3 and 4. The uniqueness of the velocity and attenuation values of particular samples of avocado fruit and its firmness may be observed by reference to FIGS. 3 and 4. These figures relate to avocado but the scope of the present invention relates also to many other fruits and vegetables. FIG. 3 shows the wave velocity changes and FIG. 4 shows the wave attenuation changes in whole avocado over a period of 8 days at room temperature compared to changes in the fruit's firmness during the same days.

In both FIGS. 3 and 4 the firmness curve during eight days is a typical representative curve for a specific variety of avocado and is considered a good predictor of the maturity of the fruit. Moreover, similar curves are described for other varieties of avocados as well.

The method for determining the quality parameters by utilizing the method and system of the present invention would be to first determine and record the acoustical parameters of several varieties and species of fruits during the ripening process as time progresses. For example, the graphs shown in FIGS. 3 and 4 represent results for avocado fruits (Persea Americana Mill., cv 'Ettinger'). Next, another fruit (7) from unknown ripening stage would be place on the housing unit (5) and brought in touch with the concentrator (4) of the transmitter (3) and the concentrator (8) of the receiver (6) and the velocity and attenuation of the unknown sample could then be determined by the computer (13). Then by comparing the velocities and attenuation computed by the computer (13) with the graphs and models of the known quality parameters of fruits, one could determine the firmness of the unknown fruits by matching its acoustical parameters as represented by its wave velocity and attenuation.

While a particular embodiment of the invention has been described above, it will be appreciated that the invention is capable of numerous arrangements, modifications and substitution without departing from the spirit of the invention. In particular, it should be noted that the analysis of velocity and attenuation of the tone burst received by the transducer (6) may be accomplished in a number of ways and correspond to several ripening behaviors. The key to the analysis is the recognition that the fruit sample will generate a signal to the receiving transducer (6) which will have acoustical information that indicates the maturity of the fruit sample.

We claim:

1. A method of determining quality parameter of fresh produce using ultrasonic sound waves, which comprises:

arranging a sample of fresh produce of an unknown maturity stage in an ultrasonic sound path;

transmitting ultrasonic sound waves along the sound path through the sample of the fresh produce;

detecting and receiving said sound waves after said sound waves pass through the fresh produce sample; and calculating values of acoustical parameters, including at least wave velocity and signal attenuation of the detected sound waves, to analyze said values which are indicative of quality of the fresh produce sample.

2. The method according to claim 1 wherein said ultrasonic sound waves are transmitted from ultrasonic transducers include the step of transmitting ultrasound from and to at least one of crystal transducers and piezoelectric transducers.

3. The method according to claim 2 wherein the transmittance of the ultrasonic sound waves is from two or more of at least one of separated transducers and coupled transducers.

4. The method according to claim 3 wherein the step of transmitting ultrasonic sound waves is changed by changing the load of the transducers on the fresh produce by varying at least one of angles of transducers used to transmit ultrasound, distances between the transducers and associated receivers, edge shape of the transducers and intensity of the sound waves.

5. A method according to claim 1 for a non-destructive determination of quality parameters in fresh produce which comprises:

(a) connecting the fresh produce of unknown maturity to two ultrasonic energy concentrators in a predetermined angle between their axes wherein one concentrator is connected to a source transducer and the other to a receiving transducer;

(b) transmitting into the produce ultrasonic sound waves from the source transducer and its energy concentrator;

(c) receiving said ultrasonic sound waves travelling through the produce by the receiving transducer connected to the energy concentrator;

(d) converting said received sound waves to electronic signals and applying said electrical signals to a pulser receiver;

(e) applying the electronic signals received in the pulser receiver to a microprocessor controlled serial interface for digitizing the electronic signal to produce a digital readout, then, analyzing the digital read out received from the microprocessor by a computer to calculate the velocity and attenuation of the ultrasonic waves in the fresh produce sample and comparing the calculated acoustical parameters to known acoustical parameters indicating known quality parameters of said fresh produce.

6. A method for determining quality parameters of fresh produce according to claim 5 wherein the fresh produce are fruits or vegetables.

7. A method for determining quality parameters of fresh produce according to claim 6 wherein the fresh produce is a whole fruit or vegetable, or tissue sample or peel of said fruit or vegetable.

8. A method for determining quality parameters of fresh produce according to claim 7 wherein the fresh produce is avocado.

9. A method for determining quality parameters of fresh produce according to claim 5 wherein the quality parameters are the firmness, ripeness, crispness and maturity.

10. A method for determining quality parameters of fresh produce according to claim 5 wherein the pulser receiver generates an electrical pulse at a frequency of about 50 kilohertz.

11. A method for determining quality parameters of fresh produce according to claim 5 wherein the electronic signals generated by the pulser receiver activate the source transducer for the production of ultrasonic waves.

12. A method for determining quality parameters of fresh produce according to claim 5 wherein the two ultrasonic energy concentrators are identical.

13. A method for determining quality parameters of fresh produce according to claim 5 wherein the two ultrasonic energy concentrators are positioned apart at a distance of approximately 5 mm and thus create the predetermined angle between them.

14. A method for determining quality parameters of fresh produce according to claim 5 wherein a cylindrical edge of the ultrasonic energy concentrators touching the sample is about 5–6 mm in diameter.

15. A method for determining quality parameters off fresh produce according to claim 5 wherein the electronic signals to be analyzed by the computers are also applied to any conventional recorder.

16. A method for determining quality parameters of fresh produce according to claim 5 wherein the electronic signals to be analyzed by the computer and compared to known acoustical parameters in graphs and models of the specific produce are to be analyzed during a maturity process of the fresh produce.

17. A method according to claim 1 wherein two or more receiving transducers are positioned at different predetermined distances for detecting the acoustical parameters.

* * * * *